United States Patent
Ohkubo et al.

(10) Patent No.: US 6,633,036 B2
(45) Date of Patent: Oct. 14, 2003

(54) ISOTOPE GAS MEASURING APPARATUS

(75) Inventors: Kunihiko Ohkubo, Moriyama (JP); Junichi Kita, Kyoto (JP); Motoo Kinoshita, Kameoka (JP); Hiroshi Nakano, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 85 days.

(21) Appl. No.: 10/078,502

(22) Filed: Feb. 21, 2002

(65) Prior Publication Data

US 2002/0134940 A1 Sep. 26, 2002

(30) Foreign Application Priority Data

Mar. 26, 2001 (JP) ........................................ 2001-086555

(51) Int. Cl.[7] ............................................. G01N 21/35
(52) U.S. Cl. ................... 250/339.13; 250/343
(58) Field of Search .............................. 250/339.13, 343

(56) References Cited

U.S. PATENT DOCUMENTS

| | | | | |
|---|---|---|---|---|
| RE33,493 E | * | 12/1990 | Lee et al. ................. | 250/343 |
| 5,543,621 A | * | 8/1996 | Sauke et al. .............. | 250/343 |
| 5,747,809 A | * | 5/1998 | Eckstrom .................. | 250/345 |
| 5,929,442 A | * | 7/1999 | Higashi .................... | 250/339.13 |
| 6,078,049 A | * | 6/2000 | Schafer et al. ........... | 250/339.09 |
| 6,202,470 B1 | * | 3/2001 | Chou ........................ | 73/24.02 |
| 6,274,870 B1 | * | 8/2001 | Kubo et al. .............. | 250/339.13 |
| 6,363,772 B1 | * | 4/2002 | Berry ....................... | 73/24.02 |
| 6,444,985 B1 | * | 9/2002 | Mori et al. .............. | 250/339.13 |

* cited by examiner

*Primary Examiner*—Albert Gagliardi
(74) *Attorney, Agent, or Firm*—Kanesaka & Takeuchi

(57) ABSTRACT

An isotope gas measuring apparatus for measuring concentrations of components in a sample gas includes two sample cells through which the sample gas passes; a control cell filled with a gas having no absorbance at a wavelength of infrared light to be measured; a light source irradiating infrared light to the sample cells and the control cell; an optical coupler for coupling light permeated from the sample cells and the control cell; a first interference filter disposed between one sample cell and the optical coupler; a second interference filter disposed between the other sample cell and the optical coupler; and an optical detector for detecting infrared light from the optical coupler. The apparatus can minimize an influence of drift, and have a simple structure.

8 Claims, 2 Drawing Sheets

ISOTOPE GAS MEASURING APPARATUS

BACKGROUND OF THE INVENTION AND RELATED ART STATEMENT

The present invention relates to an isotope gas measuring apparatus used in the medical field for measuring a stable isotope gas in an expiration gas. More particularly, the invention relates to an isotope gas measuring apparatus for determining concentrations of $^{12}CO_2$ and $^{13}CO_2$ or a ratio thereof by measuring a sample gas containing $^{12}CO_2$ and $^{13}CO_2$ by a non-dispersion-type infrared absorption method.

Heretofore, a method called an isotopic tracer technique has been used to study metabolism, storage, excretion and the like in vivo. Using an isotope labeled element or substance as a tracer, this technique is examining a behavior of the specific element or substance in vivo, which shows a similar behavior to that of an unlabeled element or substance. In the medical field, this technique has been used as a tool for diagnosis and research using a tracer with a stable isotope label without fear of exposure to radiation. More specifically, this technique has been used to diagnose an infection of Helicobacter Pylori (hereinafter referred to simply as "Pylori"), which is believed to cause a gastric duodenum and/or stomach ulcer and a gastric cancer. In this method, a urea reagent containing $^{13}C$, a stable isotope element, is used and the decomposition of the urea reagent by Helicobacter Pylori is detected by measuring an expiration gas of an examinee. The "Pylori" has a urease activity wherein urea is decomposed into carbon dioxide and ammonia. Thus, urea labeled with $^{13}C$, an isotope of $^{12}C$, is administered to an examinee, and a concentration (actually, a concentration ratio of $^{12}CO_2$ and $^{13}CO_2$) of $^{13}CO_2$ in an expiration gas of the examinee is measured. If "Pylori" is present in the alimentary system of the examinee, since the concentration of $^{13}CO_2$ becomes higher than that of a normal person who does not have "Pylori", it can be determined that the examinee is infected by "Pylori".

Generally, as a method for measuring an isotope gas (for example, $^{12}CO_2$ and $^{13}CO_2$) in a gas sample, there have been known methods using a mass spectrograph and a non-dispersion infrared spectroscopy. In a method using a mass spectrograph, although an accurate measurement can be carried out, an apparatus tends to be very expensive and requires a skilled operator. On the contrary, in a method using a non-dispersion infrared spectroscopy, an apparatus is generally inexpensive due to a simpler structure, and its operation is relatively easy. Thus, it is assumed that the method using a non-dispersion infrared spectroscopy will prevail in the future.

There are three typical methods to measure a ratio of the isotope gases $^{12}CO_2$ and $^{13}CO_2$ using a non-dispersion infrared spectroscopy.

(1) The first method uses four gas cells, i.e. a $^{12}CO_2$ measuring sample cell, a $^{13}CO_2$ measuring sample cell, two control cells filled with a gas containing $^{12}CO_2$ and $^{13}CO_2$ at a predetermined concentration for each sample cell, and two infrared detectors. In this method, a sample gas is injected into each sample cell, and absorbance of infrared light of the sample gas is compared with those of the respective control gas to determine concentrations of $^{12}CO_2$ and $^{13}CO_2$.

(2) The second method uses two sample cells with interference filters and two infrared detectors for the measurement of $^{12}CO_2$ and $^{13}CO_2$, as disclosed in Japanese Patent No. 2996611. In this method, a sample gas and a control gas are injected one by one into a $^{12}CO_2$ measuring cell and a $^{13}CO_2$ measuring cell to measure absorbance of the infrared light, and compare the absorbance of the sample gas and the control gas to measure concentrations of $^{12}CO_2$ and $^{13}CO_2$.

(3) The third method uses only two cells for a sample and a control gas and one infrared detector with a grating, as disclosed in Japanese Patent Publication (KOKOKU) No. 3-31218. In this method, the infrared light from a light source is filtered, and only the light of absorption wavelength (about 4,250 nm for $^{12}CO_2$ and about 4,415 nm for $^{13}CO_2$) is introduced into the sample cell and the control cell one by one, and absorbance of the sample gas and the control gas at the respective wavelengths are measured and compared to thereby determine the concentrations of $^{12}CO_2$ and $^{13}CO_2$.

Among the methods for measuring a ratio of $^{12}CO_2$ and $^{13}CO_2$, in the case of (1), the absorbance of the infrared light passing through the control cell and the sample cell is always compared, so that a stable measurement can be obtained. However, since the two independent systems for measuring $^{12}CO_2$ and $^{13}CO_2$ are used, they need their own infrared light sources and infrared detectors. It is known that light intensity from a light source varies with time and an output of an infrared detector with respect to the same light intensity also varies with time. The phenomena are called drift. If a variance due to the drift in two systems is not equal, even if a sample gas has the same $^{12}CO_2$ to $^{13}CO_2$ ratio, results of the two systems can be different. Also, since two detectors and two control cells are required, a cost becomes high.

The above-mentioned method (2) is called a single cell system, wherein although two infrared detectors are used, one single cell is used by switching a sample gas and a control gas. Therefore, another cell is not necessary, so that a cost of an apparatus is lower than that of the method (1). However, it is required to replace a gas in the cell with another gas in order to measure two types of gases, i.e. a sample gas and a control gas. The step of replacing a gas normally takes 1 to 3 minutes. If the drift occurs in a measuring system within this time period, an accuracy of the measurement is deteriorated by the drift and becomes worse than that of the method (1). Also, as a sample gas and a control gas are measured one by one, it takes nearly two times longer than that of the method (1).

Although the method (3) comprises only a sample cell, a control cell and an infrared detector, an optical system including a grating and a mirror for obtaining infrared light with a predetermined wavelength from an infrared light source has to be provided. Such an optical system tends to be a complicated one, which results in a higher cost of an apparatus.

The present invention has been made to obviate the above disadvantages, and an object of the invention is to provide an isotope gas measuring apparatus, wherein stable and repeatable measurement with respect to a gas concentration can be achieved without influence of the drift of a light source, an optical detector and the like. Moreover, the measuring apparatus has a simple structure and can be manufactured at a lower cost.

Further objects and advantages of the invention will be apparent from the following description of the invention.

SUMMARY OF THE INVENTION

In order to achieve the above objects, the present invention provides an isotope gas measuring apparatus to determine concentrations of carbon dioxide $^{12}CO_2$ and stable isotope $^{13}CO_2$ thereof in a sample gas by absorbance of the infrared light. The isotope gas measuring apparatus includes: two sample cells through which a sample gas to be measured passes; a control cell filled with a gas having no infrared light absorption at a wavelength used for the measurement; a light source for irradiating infrared light into the two sample cells and the control cell; an optical coupler for coupling lights passing through the two sample cells and the A comparative cell; a first interference filter disposed between the light source and the optical coupler in a light path of one of the two sample cells; a second interference filter disposed between the light source and the optical coupler in a light path of the other sample cell; and an optical detector for detecting the infrared lights from the optical coupler.

In the present invention, the isotope gas measuring apparatus uses three cells; namely a sample cell for measuring $^{12}CO_2$, a sample cell for measuring $^{13}CO_2$ and a control cell. The control cell can be common for $^{12}CO_2$ and $^{13}CO_2$. Further, the permeated light from these three cells can be coupled into one through the optical coupler to thereby reduce the number of optical detectors to one. Thus, the sample gas and the control gas can be measured substantially at the same time, which minimizes the negative influence of the drift in the light source, the optical detector and the like. Also, since the isotope gas measuring apparatus of the invention uses the same light source and detector for measuring the permeated infrared lights from $^{12}CO_2$ and $^{13}CO_2$ and the control gas, the drift between the gases can be removed. Further, since the isotope gas measuring apparatus of the invention uses only three cells and one detector, a structure thereof is simple, and a cost thereof can be lowered when compared with those of the above-stated three methods.

The permeated lights from the $^{12}CO_2$ measuring sample cell, the $^{13}CO_2$ measuring sample cell and the control cell are coupled through the optical coupler and its absorbance is measured by the detector. A signal from each of the cells can be taken by providing a separator circuit to a processing circuit that processes a signal from the detector. For this purpose, in the case that a flashing light source is used as an infrared light source, a timing of the emission is regulated; and when a continuous emission light source and a mechanical rotating sector are used, a switching timing of the light is to be controlled.

DETAILED DESCRIPTION OF THE PREFERRED EMBODIMENTS

Figure 1:
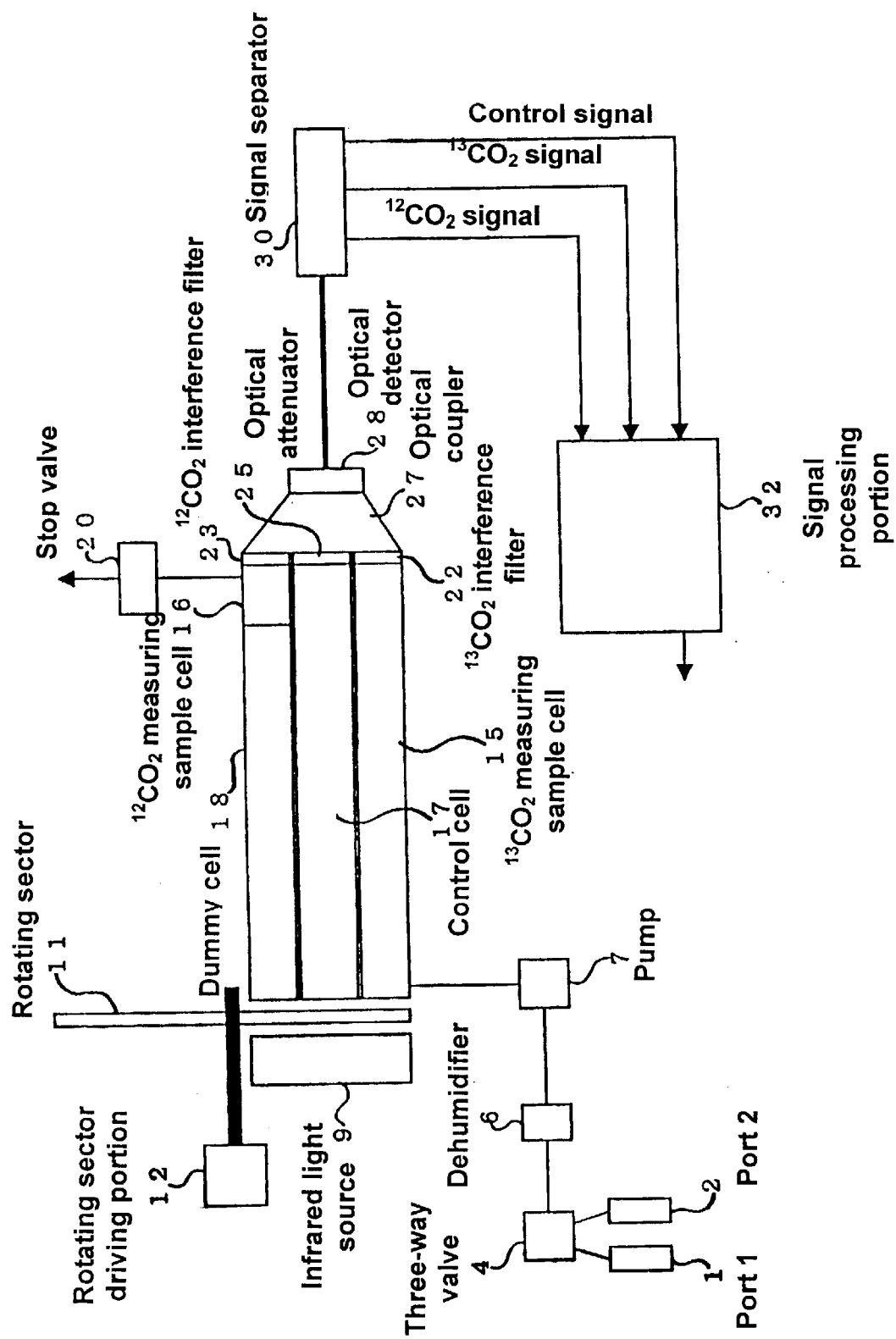
FIG. 1 is a block diagram of an embodiment of an isotope gas measuring apparatus for diagnosing Pylori infection according to the present invention.

Hereunder, embodiments of the present invention will be described in detail with reference to the accompanying drawings. FIG. 1 is a block diagram showing a structure of an embodiment of an isotope gas measuring apparatus according to the present invention for diagnosing Pylori infection. The diagnosis of Pylori infection is carried out such that a urea reagent labeled with $^{13}C$ is orally administered to an examinee, and expiration gases of the examinee before and after the administration of the reagent are measured. If Pylori are present in the stomach of the examinee, the urea reagent is decomposed by Pylori to produce $^{13}CO_2$ that enters the blood and is discharged as expiration gas. Thus, concentration of $^{13}CO_2$ and $^{12}CO_2$ in the expiration gas is measured and a ratio thereof is compared. In this apparatus, the ratios of $^{13}CO_2$ and $^{12}CO_2$ in the two sample gases are measured, respectively, and a difference between the ratios of the two sample gases is output.

The isotope gas measuring apparatus for diagnosing Pylori infection according to the present invention includes a port 1 to which a gas bag (not shown) containing a control expiration gas sample before administration of a reagent is attached; a port 2 to which a gas bag (not shown) containing an expiration gas sample after administration of a reagent is attached; a three way valve 4 for switching the port 1 and the port 2; a dehumidifier 6; a pump 7; a $^{13}CO_2$ measuring sample cell 15; a $^{12}CO_2$ measuring sample cell 16; a control cell 17; a dummy cell 18; and a stop valve 20. Further, the apparatus includes an infrared light source 9 for irradiating infrared light to the $^{13}CO_2$ measuring sample cell 15, the $^{12}CO_2$ measuring sample cell 16, the control cell 17 and the dummy cell 18; a rotating sector 11; and a rotating sector driving portion 12. Furthermore, the apparatus is formed of a $^{13}CO_2$ interference filter 22, a $^{12}CO_2$ interference filter 23, and an optical attenuator 25, respectively disposed in a permeated light path from the $^{13}CO_2$ measuring sample cell 15, the $^{12}CO_2$ measuring sample cell 16 and the control cell 17; an optical coupler 27; a light detector 28; a signal separator 30; and a signal processing portion 32.

Next, an operation of the apparatus will be explained. First, the gas bag (not shown) containing a control expiration gas sample before the administration of the reagent is attached to the port 1, and the gas bag (not shown) containing an expiration gas sample after the administration of the reagent is attached to the port 2. When the three-way valve 4 is switched so that the port 1 can communicate, the control expiration gas sample before the administration of the reagent is sucked through the pump 7. The dehumidifier 6 dries the sample gas by controlling a temperature of the sample gas at a predetermined dew point. Since an expiration gas tends to contain a saturated vapor in the vicinity of a room temperature, the expiration gas sample needs to be dehumidified to protect the optical system from condensation and, at the same time, a humidity of the sample gas is maintained at a constant level. The sample gas passing through the dehumidifier 6 is pushed into the $^{13}CO_2$ measuring sample cell 15 through the pump 7. The sample gas passing through the $^{13}CO_2$ measuring sample cell 15 is introduced into the $^{12}CO_2$ measuring sample cell 16 to be discharged through the stop valve 20. The stop valve 20 is closed while the measurement is not carried out to thereby prevent moisture and dust from penetrating from outside thereinto.

Figure 2:
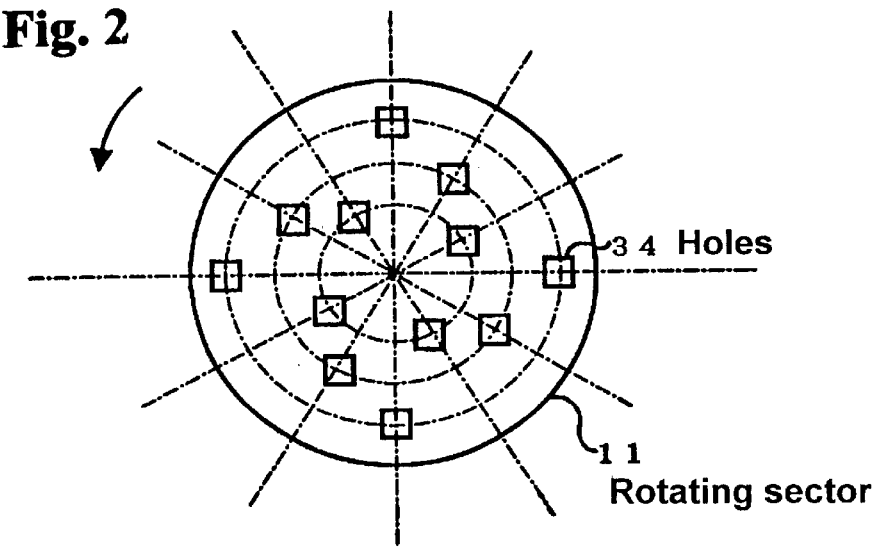
FIG. 2 is a diagram showing a structure of a rotating sector.
Figure 3:
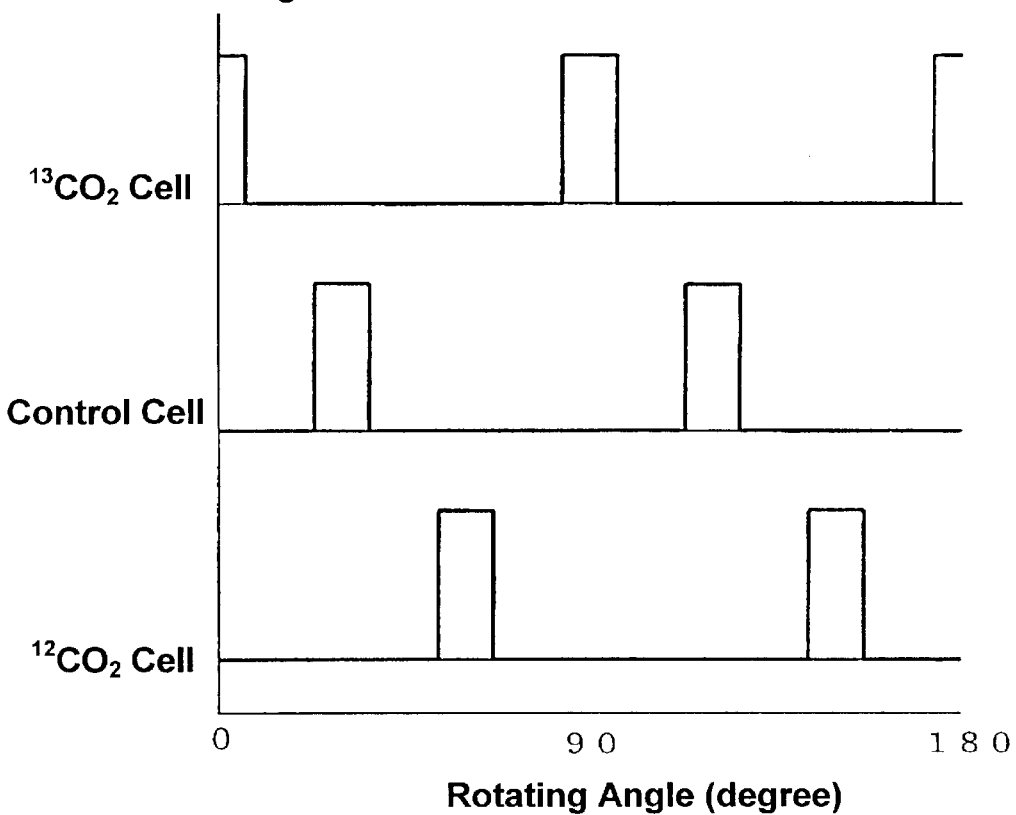
FIG. 3 is a graph showing a relationship between a rotating angle of the rotating sector and incident light to a $^{13}CO_2$ measuring sample cell, a $^{12}CO_2$ measuring sample and a cell control cell, respectively.

The infrared light source 9 irradiates infrared light to the $^{13}CO_2$ measuring sample cell 15, the $^{12}CO_2$ measuring sample cell 16, the control cell 17 and the dummy cell 18, respectively. The infrared light source 9 uses a ceramic heater as a light source, to and the ceramic heater kept at a temperature in the vicinity of 1,000° C. irradiates the infrared light. The rotating sector 11 rotated by the rotating sector driving portion 12 switches on and off the infrared light entering the respective cells. FIG. 2 shows a structure of the rotating sector 11. The rotating sector 11 has a plurality of holes 34, as shown in FIG. 2, so that the infrared light passes through the respective cells and then enters the optical detector through the optical coupler 27 in a predetermined order. FIG. 3 shows relationships between the incident light to the respective cells and a rotating angle of the rotating sector 11. The rotating sector 11 rotates at 4,000 rotation per minute, and each of the permeated light from the $^{13}CO_2$ measuring sample cell 15, the $^{12}CO_2$ measuring sample cell 16 and the control cell 17 is measured in a predetermined order. Since a measurement interval is very short, such as less than 0.01 second, an influence of the drift in the infrared light source 9 and the light detector 28 is negligible.

Although the sample is an expiration gas containing 2 to 5% $CO_2$, since $^{13}CO_2$ and $^{12}CO_2$ have different concentrations (1 to 100 ratio), a measurement range of each gas is different. As the $^{13}CO_2$ concentration is lower, the optimum length of the $^{13}CO_2$ measuring sample cell 15 becomes longer and is limited by the length of the apparatus. On the other hand, the $^{12}CO_2$ concentration is higher and the length of the $^{12}CO_2$ measuring sample cell 16 is set around 5 mm. Since the lengths of the $^{13}CO_2$ measuring sample cell 15 and the $^{12}CO_2$ measuring sample cell 16 are different, the dummy cell 18 is disposed in a dead space of the $^{12}CO_2$ measuring sample cell 16. Nitrogen gas that does not absorb the infrared light is filled under one atmospheric pressure in the dummy cell 18. The nitrogen gas is also filled in the control cell 17 under one atmospheric pressure in the same manner as in the dummy cell 18.

Since an absorption of the each gas is determined at the $^{13}CO_2$ measuring sample cell 15 and the $^{12}CO_2$ measuring sample cell 16, the interference filter 23 and the interference filter 22 for selectively permeating adsorption wavelengths at about 4,250 nm for $^{12}CO_2$ and about 4,415 nm for $^{13}CO_2$ are disposed between the optical coupler 27 and the respective cells. Since the infrared light intensity becomes extremely small due to the interference filters 22 and 23, the optical attenuator 25 is provided between the comparative cell 17 and the optical coupler 27 to thereby provide the same light intensity as those of the $^{13}CO_2$ measuring sample cell 15 and the $^{12}CO_2$ measuring sample cell 16.

The permeated lights from the respective cells are coupled by the optical coupler 27 and reach the optical detector 28. PbSe is used as the light detector 28. The wavelength selectivity and sensitivity of PbSe have a temperature dependency, so that PbSe is cooled down to −20° C. where the light detector has strong sensitivity at the absorption band of $CO_2$. The permeated lights from the respective cells reach the optical detector 28 in the order of the $^{13}CO_2$ measuring sample cell 15, the comparative cell 17 and the $^{12}CO_2$ measuring sample cell 16 as shown in FIG. 3. Since the signals from the optical detector 28 are arranged in the order of the signals from the three cells, the signals can be divided into three signals at the signal separator 30 by separating the signals with time. These signals are processed at the signal processing portion 32 using algorithm such as -Ln ($^{13}CO_2$ signal/control signal) and -Ln ($^{12}CO_2$ signal/control signal), and are converted into a $^{13}CO_2$ to $^{12}CO_2$ concentration ratio from a standard line obtained in advance.

After the control expiration gas sample before the administration of the reagent is measured, the three-way valve 4 is switched so that the port 2 can communicate. The expiration gas sample after the administration of the reagent is then sucked through the pump 7, and measurement thereof is carried out in the same manner as described above. The difference between the ratios of the $^{13}CO_2$ concentrations and the $^{12}CO_2$ concentrations from a result of the control expiration gas sample before the administration of the reagent and the expiration gas sample after the administration of the reagent is calculated and output to thereby complete the measurement.

In the above embodiment, the holes 34 of the rotating sector 11 are formed so that a switching pattern of the infrared from the respective cells is based on time. It is also possible to switch the infrared light from the respective cells based on a frequency of switching on and off the infrared light irradiated to the respective cells. For example, a pattern of the holes 34 of the rotating sector 11 may be formed such that irradiation to the $^{13}CO_2$ measuring sample cell 15 is carried out in 1,000 Hz, irradiation to the $^{12}CO_2$ measuring sample cell 16 is carried out in 100 Hz, and irradiation to the comparative cell 17 is carried out in 10 Hz.

Hereinabove, although the embodiment according to the present invention has been explained, the present invention is not limited thereto. The present invention can be modified within the scope of the claims. For example, instead of using PbSe as the detector 28 in the present embodiment, the detector 28 is not limited thereto and, for example, a pyroelectric type sensor such as DLATGS, a goley cell and the like can be used. Also, in the above embodiment, the continuous emission ceramic heater is used as the infrared light source 9 in combination with the rotating sector 11. However, a flashing light source, such as an infrared light-emitting diode (LED), an infrared laser diode (LD) and a lamp, can also be used. In this case, a flashing light source is disposed in each cell, so that the rotating sector is not required. When a flashing light source is used, it is possible to separate signals from the respective cells by changing a flashing frequency of the flashing light source.

It is also possible to elongate the $^{12}CO_2$ measuring sample cell 16 by omitting the dummy cell 18. Further, in the above embodiment, although the infrared light source 9 has a large irradiation area, if a variation of light intensity with a location of the infrared light source becomes an issue, the similar apparatus to the optical coupler 27 may be provided on the side of the infrared light source, and the infrared light source with a small irradiation area may be used.

According to the present invention, since only one light detector is used because of coupling the permeated lights from the three cells through the optical coupler, a sample gas and a control gas can be measured at substantially the same time. Thus, there is substantially no influence of the drift in the light source, the optical detector and the like. Also, since the same light source and the same optical detector for measuring the permeated lights from $^{12}CO_2$, $^{13}CO_2$ and the control gas are used, the drift with respect to the isotopic ratio is also eliminated. Further, since only three cells and one detector are needed, a structure of the measuring apparatus is simple and its cost can be reduced.

While the invention has been explained with reference to the specific embodiments of the invention, the explanation is illustrative and the invention is limited only by the appended claims.

What is claimed is:

1. An isotope gas measuring apparatus for measuring concentrations of different components in a sample gas, comprising:

first and second sample cells through which said sample gas passes;

a control cell filled with a gas having no absorbance at a wavelength of infrared light to be measured;

a light source for irradiating infrared light to the first and second sample cells and said control cell;

an optical coupler connected to the first and second sample cells and the control cell for coupling lights from the first and second sample cells and the control cell;

a first interference filter disposed between the first sample cell and the optical coupler for allowing one particular wavelength of the light source for measuring one of the components to pass therethrough;

a second interference filter disposed between the second sample cell and the optical coupler for allowing another particular wavelength of the light source for measuring another of the components to pass therethrough; and an optical detector connected to the optical coupler for sequentially detecting lights from the optical coupler.

2. An isotope gas measuring apparatus according to claim 1, wherein said first interference filter allows the wavelength to measure carbon dioxide $^{12}CO_2$, and said second interference filter allows the wavelength to measure carbon dioxide $^{13}CO_2$.

3. An isotope gas measuring apparatus according to claim 1, further comprising a rotating sector disposed between the light source and the first and second sample cells and the control cell for switching on and off the infrared light from the light source entering the sample cells and the control cell.

4. An isotope gas measuring apparatus according to claim 1, wherein said first interference filter selectively permeates infrared light of a wavelength at about 4,250 nm and said second interference filter selectively permeates infrared light of a wavelength at about 4,415 nm.

5. An isotope gas measuring apparatus according to claim 1, wherein said second sample cell includes a cell through which the sample gas passes and a cell filled with an inert gas.

6. An isotope gas measuring apparatus according to claim 1, wherein said optical detector is made of PbSe.

7. An isotope gas measuring apparatus according to claim 1, wherein said optical detector is a pyroelectric sensor.

8. An isotope gas measuring apparatus according to claim 1, wherein said optical detector is a goley sensor.

* * * * *